United States Patent [19]
Frank

[11] 3,942,513
[45] *Mar. 9, 1976

[54] RESPIRATORY DISTRESS STIMULATOR SYSTEM

[75] Inventor: Ulrich Anton Frank, Princeton, N.J.

[73] Assignee: Hoffmann-La Roche Inc., Nutley, N.J.

[ * ] Notice: The portion of the term of this patent subsequent to Mar. 5, 1991, has been disclaimed.

[22] Filed: Jan. 28, 1974

[21] Appl. No.: 436,395

Related U.S. Application Data

[63] Continuation-in-part of Ser. No. 239,264, March 29, 1972, Pat. No. 3,795,240.

[52] U.S. Cl. ......... 128/2 R; 128/DIG. 29; 128/2.08; 128/28; 340/279
[51] Int. Cl.² ........................................ A61B 5/08
[58] Field of Search ............. 128/2.08, 2 S, 2 R, 28, 128/33, 1 B, DIG. 29; 340/279

[56] References Cited
UNITED STATES PATENTS

| | | | |
|---|---|---|---|
| 2,776,658 | 1/1957 | Gibbon | 128/28 |
| 3,085,568 | 4/1963 | Whitesell | 128/33 |
| 3,392,723 | 7/1968 | Calvin | 128/33 X |
| 3,547,106 | 12/1970 | Bornmann | 128/2 S |
| 3,631,438 | 12/1971 | Lewin | 128/2 S X |
| 3,672,354 | 6/1972 | Weber | 128/33 |
| 3,730,173 | 5/1973 | Deaton | 128/2.08 |
| 3,795,240 | 3/1974 | Frank | 128/2.08 X |

OTHER PUBLICATIONS

Frank, U. A. et al., Pediatrics, Vol. 51, No. 5, May, 1973, pp. 878–883.

*Primary Examiner*—Kyle L. Howell
*Attorney, Agent, or Firm*—Samuel L. Welt; Bernard S. Leon; Mark L. Hopkins

[57] ABSTRACT

A patient care system for monitoring respiratory distress problems and providing therapeutic treatment comprising, a sensor for generating patient derived respiratory activity signals, detecting an apnea episode from the signals, and providing in response to a detected apneic episode, stimulation of the patient by a momentary inflation or deflation of a pneumatic means adapted for placement under the patient to raise or lower the patient and induce thereby a loss of equilibrium for startling the patient into a natural respiration pattern.

16 Claims, 11 Drawing Figures

RESPIRATORY DISTRESS STIMULATOR SYSTEM

CROSS-REFERENCE TO RELATED APPLICATION

This is a continuation-in-part of application Ser. No. 239,264, filed Mar. 29, 1972, now U.S. Pat. No. 3,795,240, issued Mar. 5, 1974.

BACKGROUND OF THE INVENTION

The present invention relates to an apnea monitoring and therapeutic system and more specifically a system directed at stimulation of a patient in respiratory distress.

The cessation of respiration or the inability to get one's breath often referred to as apnea, is a serious problem which becomes dangerous especially in premature infants where such occurrences are frequent. It is understood that repeated attacks as well as prolonged attacks of apnea are factors which carry a poor prognosis both for life and for subsequent mental development resulting from irreversible cerebral damage sustained during these apneic episodes. The best prospect of reducing harmful effects of late-occurring apnea is through constant surveillance preferably using some automated device to alert attendants so that stimulation through resuscitation can begin promptly. As a consequence, apnea monitoring of premature infants has become an accepted practice in most institutions.

Management of apnea monitoring in the newborn, particularly in prematures, for the most part includes sensitive devices for detecting apneic events. Upon detection of an apneic episode a visual or audible alarm is generated, to call the attending nurse for prompt manual stimulation of the infant in an attempt to terminate the episode by restoring normal breathing. Alertness and responsiveness of the nursing staff is important as it becomes more difficult to obtain a positive response to stimulation the longer the apnea persists. Naturally then, most apnea monitors are designed to provide an early alarm. Unfortunately, however, most of these apneic episodes are of a short duration and occur almost randomly during any day of neonatal life. Thus, they place an unnecessary burden on the nurse to the extent that in some cases it is conceivable that the alarms may even be neglected. There is a further difficulty inherent in the operation of most monitors. Breathing signals from the infant vary in amplitude and need to be adjusted for each infant. Unfortunately the signal also varies as the infant moves. Yet if the nurse adjusts sensitivity too high, heart beats are interpreted as breathing, with disasterous results. If the sensitivity is too low, shallow breathing triggers a false alarm, much to the annoyance of attending personnel.

In the instant case, these difficulties are avoided by adjustment of the device on the low side of sensitivity; former false alarms are now unnecessary stimulations. This tends to lessen the number of manual intrusions required by attending personnel, thereby attaching greater validity and importance to alarms.

The purpose of the present invention is to avoid some of the problems incurred in apnea monitoring by closing the loop of the automated monitoring system, to provide a therapeutic action by early stimulation of the respiratory distressed patient. The preferred innovative technique of automatic mechanical stimulation in the present embodiment is directed to suddenly induce a loss of equilibrium, for example, such as from a falling sensation to, in effect, startle the infant into a natural respiration pattern. This is conveniently accomplished by sudden inflation or deflation, through regulating the pneumatic pressure, of a small pneumatic mattress which is preferably placed under the upper half of the infant's body.

PREFERRED EMBODIMENTS OF THE INVENTION

Figure 1:
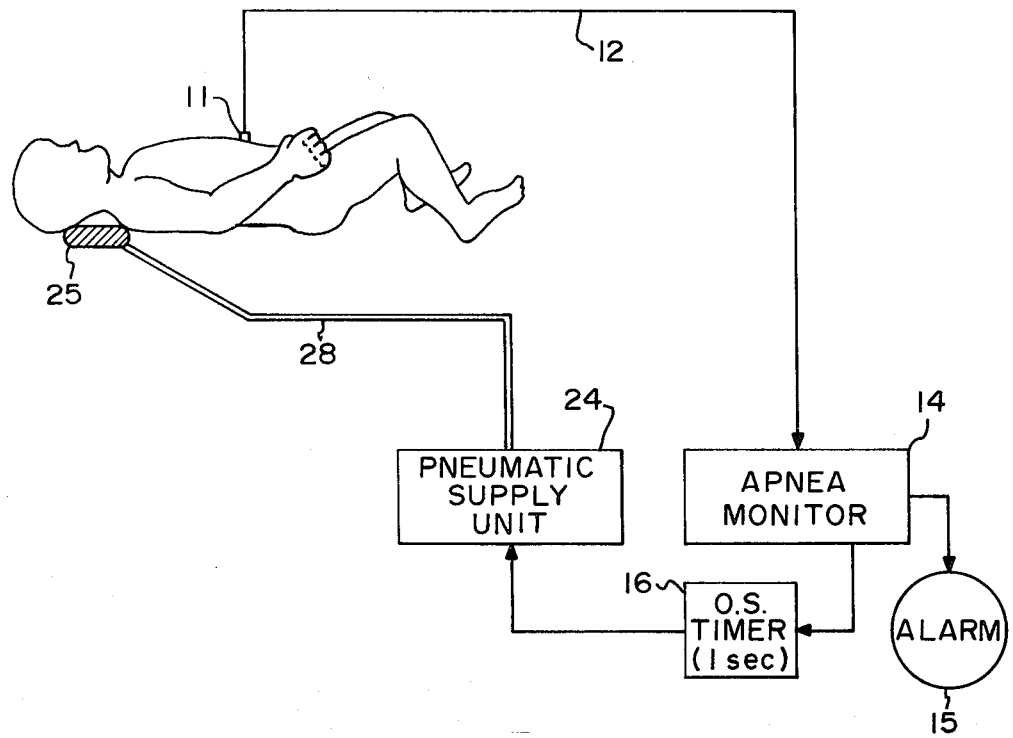
FIG. 1 is a schematic diagram in block form of the invention.

With reference to the drawings there is shown in FIG. 1 a preferred embodiment of the invention comprising a sensor 11 secured by suitable means to a patient, the respiratory activity detected by sensor 11 being converted to electrical signals which are conducted by lead 12 to an apnea monitor 14. Respiratory distress problems are detected from the respiratory signals by an apnea monitor 14 to emit signals indicative of apnea episodes for energizing an alarm 15 and for activating a one shot unit 16 serving as a one second timer in the present embodiment.

Figure 2:
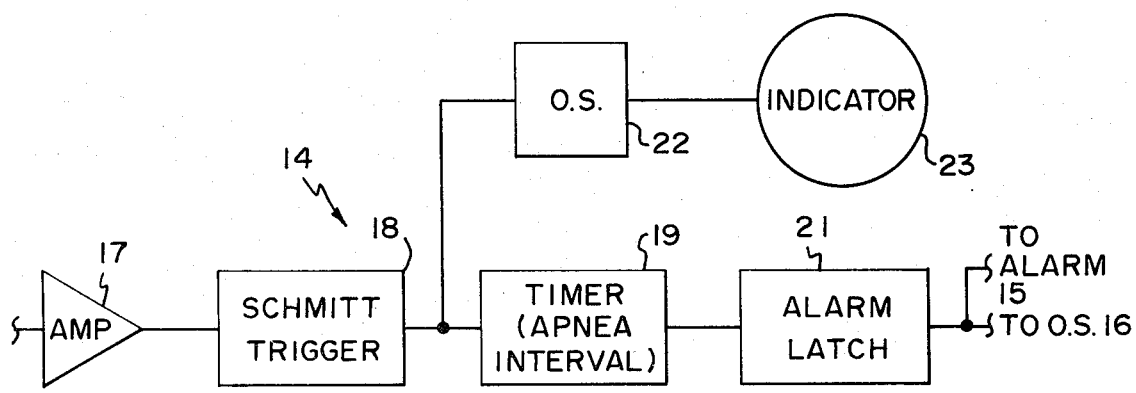
FIG. 2 is a schematic diagram in block form of a typical apnea monitor 14 illustrated in FIG. 1.

The apnea monitor 14 could take the configuration of a number of conventional apnea monitors now commercially available irrespective of whether the basis of their operation is based on the impedance pneumography, capacitance respirometry, or any other technique for detecting the apneic episode. A typical one of such apnea monitors is shown in FIG. 2 including, an input amplifier 17 which is driving a Schmitt trigger 18 adapted to be responsive during the period its input signal penetrates above a predetermined threshold level for which the Schmitt trigger is set. The Schmitt trigger output is connected to a timer 19 having a timing capacitance which will react in response to a predetermined interval for denoting an apnea interval to in turn produce an output for exciting an alarm latch 21, the output of which is connected to the one shot unit 16, illustrated in FIG. 1. The Schmitt trigger 18 output is also used for energizing a one shot unit 22 which in turn drives an indicator 23 representative of the respiration activity of the patient.

With reference back to FIG. 1, the duration of the one shot timer 16 will determine the period during which stimulation is to be applied to the patient. The one shot timer 16 is connected for driving a pneumatic supply unit which in turn is pneumatically coupled through suitable tubing to an inflatable pneumatic stimulator 25 placed under the patient. In a situation wherein a patient is having an apneic episode, the pneumatic stimulator is momentarily inflated or momentarily deflated to induce a sudden loss of equilibrium which, in effect, startles the patent back into a normal respiration pattern. The reader is referred to the article appearing in Pediatrics, Vol. 51, No. 5, May 1973 at pages 878–883 coauthored by this inventor entitled "Treatment of Apnea in Neonates With an Automated Monitor-Actuated Apnea Arrestor."

Figure 3A:
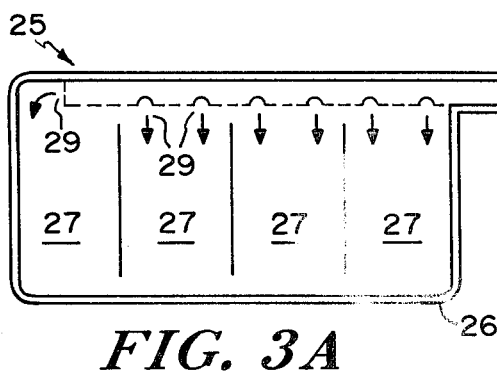
FIG. 3A is a top plan view of one embodiment of a pneumatic stimulator 25 shown in FIG. 1.

An embodiment of the pneumatic stimulator is illustrated in FIG. 3A wherein a rectangular shaped inflatable mattress-like arrangement is provided which is comprised of a flexible casing 26 constructed of, for example, an elastomeric material which might be rubber, neoprene, polyethylene vinyl, etc. While the specific shape of stimulator 25 is shown being rectangular in FIG. 3A, it is to be understood that other shapes are not to be excluded under the scope of this invention. The shape of the stimulator may, in fact, be predeterminable depending on the situation on hand or in mind, and may be elliptical or perhaps somewhat specially shaped to conform, for example, to the nape of the neck of a neonate. The particular pneumatic stimulator shown FIG. 3A has an air mattress configuration with four partially separated areas 27 each of which is supplied with air through a relatively rigid tube 28 via apertures 29 therein. The tube 28 is advantageous in that because of its relative rigidity, the air mattress cannot be folded or bent-over at an area where one depends on the passage of air through the several segments for proper air flow. Otherwise, as is experienced with conventional air mattresses, when folded over the continuity of air flow is obstructed between adjacent segments to prevent the air mattress from being completely and uniformly inflated. By use of the tubular mattress construction, the height of the mattress when fully inflated can be better regulated over the entire area of the mattress, and thus prevent the pneumatic stimulator from billowing up when inflated to otherwise possibly cause the patient to be moved to one side. A normal size of the air mattress for an infant might be about 5 by 8 inches to allow for considerable movement of the neonate without having the head and neck slide off when used under the head and neck.

Figure 3B:
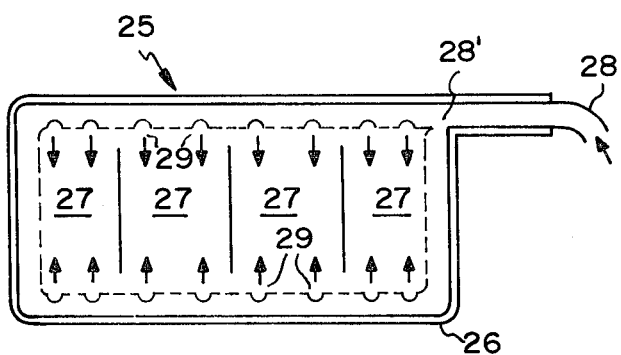
FIG. 3B is a top plan view of another embodiment of a pneumatic stimulator 25.

Referring to FIG. 3B, there is illustrated therein an alternative embodiment of pneumatic stimulator 25. In this instance, the relatively rigid tube 28 extends so as to form a continuous loop around the inner periphery of the casing 26. This arrangement provides for the apertures 29 to be located on opposite sides of the loop so as to permit direct inflation of the chambers 27 from both ends thereof simultaneously, and thus, to ensure a more uniform and rapid inflation of the mattress. This closed-loop configuration is made possible by use of a Y-junction 28', which preferably is situated within the interior of the casing 26 as shown in FIG. 3B, but which may alternatively be provided just outside the mattress interior. It is, moreover, preferable that the Y-junction be situated in one corner of the mattress for a rectangular mattress configuration. This preference, of course, becomes moot in, for example, an elliptical configuration.

As a consequence of the fact that the mattress configuration of FIG. 3B (as is the case with the embodiment depicted in FIG. 3A) is such as to have its sections or compartments situated progressively farther away from the air inlet as represented by the point of entry of the rigid tubing into the stimulator 25 interior, uniform inflation (and deflation) of the stimulator 25 may require that the apertures 29 be progressively larger in diameter relative to the distance thereof from the air inlet. Moreover, since the air inlet is in FIG. 3B represented by the Y-junction, and the lower row of apertures is, in terms of tube length, farther from the air inlet, each aperture of the lower row may be provided with a correspondingly larger diameter than its counterpart in the upper row of apertures.

Figure 3C:
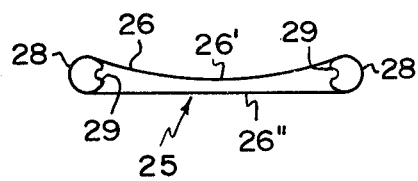
FIG. 3C is a cross-sectional view of an embodiment of a pneumatic stimulator similar to that depicted in FIG. 3B.

FIG. 3C is a cross-sectional view of a mattress embodiment similar to that depicted in FIG. 3B, wherein the tube extending around the periphery of the mattress in this embodiment actually constitutes a portion of the mattress exterior itself. In particular, the casing 26, which may be made, for example of an elastomeric material such as polyvinylchloride, may actually be comprised of a top piece 26', and a bottom piece of identical material 26". These two pieces may be sealably mated to the rigid tube 28 by means of heat sealing techniques. Thus, it may be seen that in addition to providing a means for conducting air into the interior of the mattress, the tube 28 forms a portion of the mattress exterior. The configuration of pneumatic stimulator 25 illustrated in FIG. 3C is, of course, depicted in the deflated mode. As is the case with the mattress embodiments depicted in FIGS. 3A and 3B, pin holes either in the casing material 26 or the tube 28 itself of the FIG. 3C arrangement do not significantly detract from the overall effective operation of the stimulator device 25. It may be that the relatively rigid tube could be somewhat uncomfortable for a patient lying on the mattress when the same is deflated in the normal or rest mode. It is, therefore, considered to be equally effective and well within the scope of this invention to have a suitably shaped mattress under the neck of a neonate in a comfortably inflated rest or normal mode. Rapid deflation thereof would just as surely cause the startling stimulus needed in the form of a falling sensation. As the rest mode in this instance is a uniformly inflated mattress, the operator may ensure from the outset that the mattress is unwrinkled or folded and thus ensure deflation. It is, therefore, possible that via this mode of operation, the elimination of the potential mild discomfort of the relatively rigid tube has also enabled a greater assurance of uniform pneumatic action within the mattress. The potential discomfort of the relatively rigid tube may substantially alternatively be lessened, particularly in the operative mode wherein the stimulator 25 is initially deflated, through the use of relatively rigid tubing of decided elliptical cross-section.

Figure 4A:
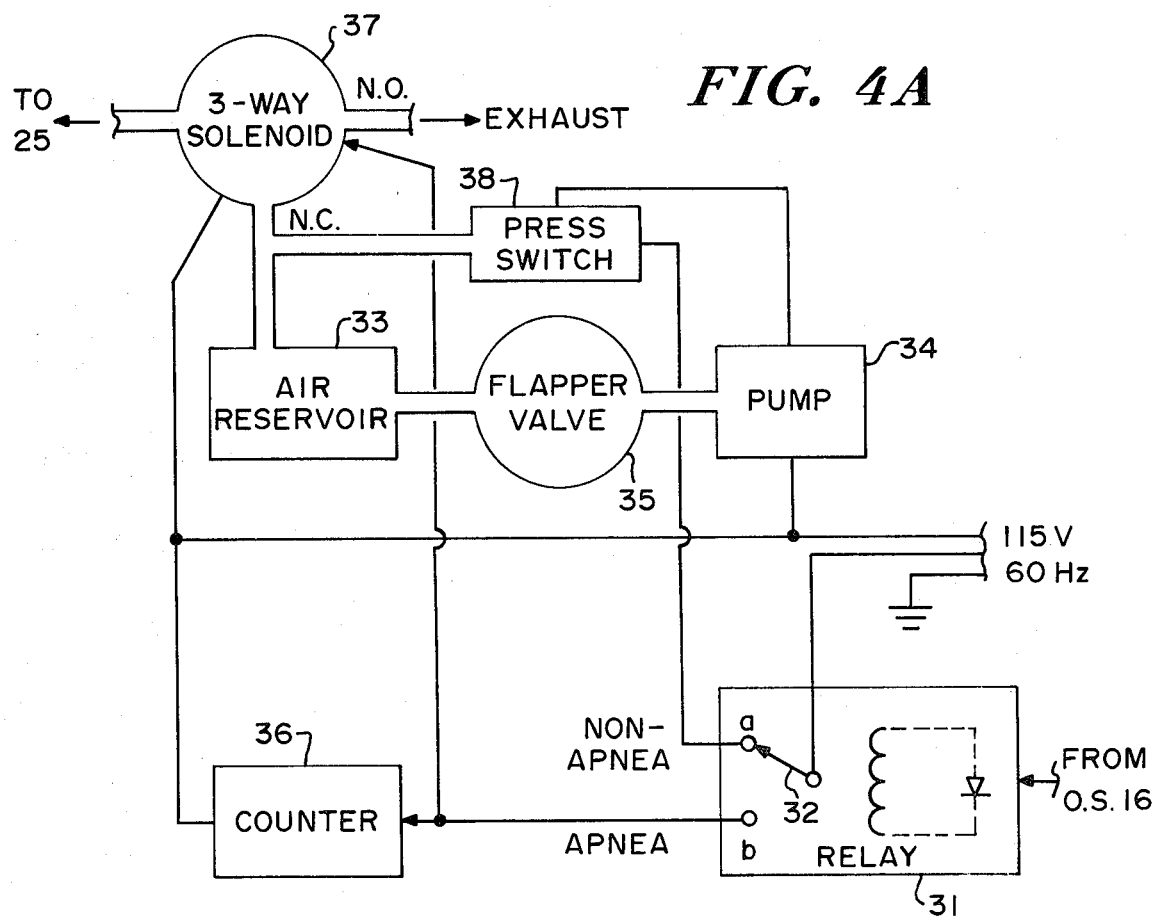
FIG. 4A is a schematic diagram in block form of a preferred embodiment of the pneumatic supply unit 24 depicted in FIG. 1.

An embodiment of the pneumatic supply unit 24, is shown in FIG. 4A, wherein the input signal from one shot 16 is connected to a relay 31 which controls a relay arm 32 to be either connected to a first terminal (a) denoted as a non-apnea terminal of a second terminal (b) denoted as an apnea terminal. It is normally assumed (rest) position the relay arm 32 is connected to terminal (a) which, in turn, is connected to a pressure switch 38. Switch 38, in turn, is connected into a section of pneumatic tubing leading from a gas (preferably air) reservoir 33 and is electrically connected to a pump 34. Air reservoir 33 and pump 34 are pneumatically connected via flapper valve 35. With relay arm 32 in its normal condition (a) the pressure switch 38 senses the pressure in air reservoir 33 which, if below a predetermined pressure level, will be supplied with pressurized air from pump 34 through one-way flapper valve 35. In case of a diaphragm or similar pump, the flapper valve 35 may be omitted.

The terminal point (b) of relay 31 is connected via an apnea lead to a counter 36 and to a three-way solenoid valve 37, the latter of which is pneumatically coupled between air reservoir 33 and the pneumatic stimulator 25 and additionally is provided with an exhaust opening. Reservoir 33 assures the availability of a rather large quantity of pressurized air to momentarily inflate the pneumatic stimulator, and also avoids delay during the inflation cycle of the pneumatic stimulator. In the present embodiment the time to inflate the pneumatic stimulator takes less than one-half second assuming a 15 psi reservoir pressure source and ¼ inch diameter connecting the tube with a final 4 psi system pressure, including the stimulator.

In operation, since relay arm 32 is normally connected to the (a) terminal, pump 34 will be charging air reservoir 33 through the flapper valve 35 during periods when the pressure switch 38 senses approximately 10% below a predetermined pressure for the air reservoir. Respiratory movements which are detected by sensor 11 (FIG. 1) are fed to the apnea monitor 14. Upon detection of an apneic episode, the one shot timer 16 is activated.

Relay 31 of FIG. 4A is activated from the one-shot unit 16 for a period of 1 second during which time relay arm 32 enables power to be supplied to the three-way solenoid valve and an apneic episode count is made on counter 36. The three-way solenoid valve is open allowing the air from reservoir 33 to momentarily inflate pneumatic stimulator 25 to stimulate the patient by suddenly raising the patient up in the air to induce a sudden loss of equilibrium and, in effect, startle the patent into normal respiration. At the end of the 1-second period relay arm 32 goes back to terminal (b). There results a return to the normal or rest mode of the three-way valve and a corresponding closing off of the path provided by the threeway solenoid valve from air reservoir 33 to the pneumatic stimulator 25, as well as an opening of the exhaust port of the threeway valve to the pneumatic stimulator 25 for deflating the latter. Because air has been used from the air reservoir 33, this will be sensed by the pressure switch 38 which will activate the pump 34 to in turn provide pressurized air in the air reservoir 33 via the flapper valve 35, to, in effect, set the system up ready for the next apnea episode when it is detected. While relay arm 32 is in the b position, it is intended that this render pressure switch 38 and, therefore, pump 34, inactive during the 1-second inflation period of the mattress.

If desired, when the stimulation is found to be successful in breaking the apneic episode, a continuing alarm may be provided until the patient is attended to or a second and possibly different-sounding nurse's alarm might be initiated within a 5-second period or any other prescribed time period that would be suitable for providing such a second alarm.

Figure 4B:
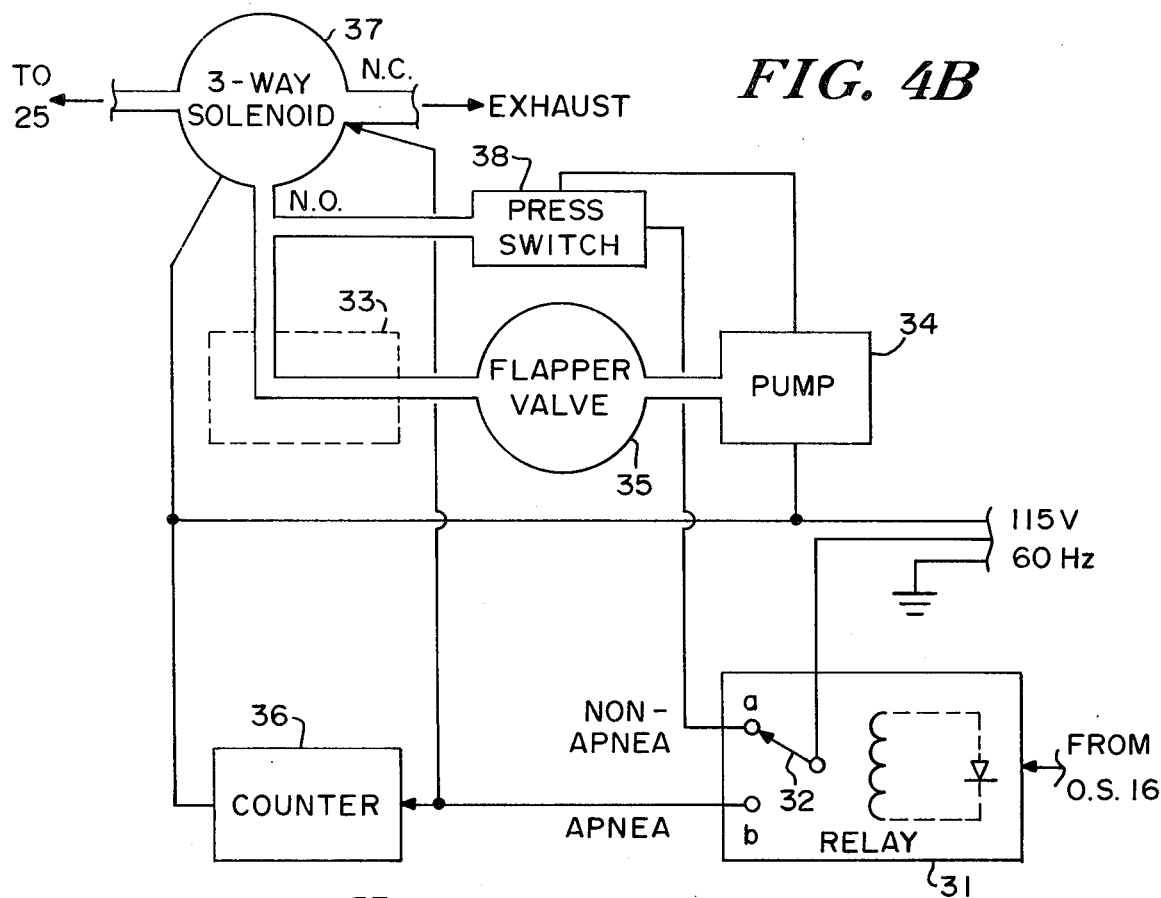
FIG. 4B is a schematic diagram in block form of another preferred embodiment of the pneumatic supply unit 24 depicted in FIG. 1.

Reference is now made to FIG. 4B, wherein the alternative situation is depicted of having a normally inflated mattress under the neonate which is intended to be momentarily deflated in causing the requisite stimulation. In this instance, it is intended that the mattress which is normally inflated to a predetermined level be deflated for a predetermined time such as the one-second period provided by one-shot 16. The initial inflation of the mattress may be maintained by having the stimulator device 25 normally coupled to the air reservoir 33 through the normally open port of three-way solenoid arrangement 37. In this way, when an apneic condition is detected and switch 32 is thrown to the b position in response thereto, the three-way solenoid 37 responds to couple the predeterminably inflated stimulator 25 to its exhaust port and thus permit a deflation of the mattress. Following the one-second interval provided by one-shot 16, switch 32 returns to the non-apnea or a position and, thus, three-way solenoid 37 returns to its normal or rest mode wherein the stimulator mattress 25 is once again coupled to air reservoir 33. In the meantime, pressure switch 38 would have sensed a decrease in pressure in the pneumatic line leading to the normally open port of three-way solenoid 37. However, since the switch 32 was momentarily in the b position, as described hereinbefore, pressure switch 38 was inhibited thereby. Now that switch 32 has returned to the non-apnea or a position, pressure switch 38 is supplied with power, and in view of the decrease in pressure being sensed, pressure switch 38 fires, thus causing pump 34 to restore pressure via flapper valve 35 to the air reservoir 33 and correspondingly reinflate the stimulator mattress 25. When pressure switch 38 again senses that the predetermined pressure of the normally-inflated mattress is restored, it shuts down, leaving thereby the system in its normal or preset mode for a follow-up stimulation activity. Now, if and when relay 31 is again actuated and switch 32 goes to position b, counter 36 would correspondingly be updated and three-way solenoid 37 would again change its coupling so as to connect mattress 25 to the exhaust port and allow the mattress to deflate rapidly.

The consideration is made of the possibility that the weight of the neonate together with an exhaust port of only normal size may not provide sufficiently rapid deflation to yield the requisite startling effect on the neonate. This hypothetical problem situation may, however, be rectified by enlarging the exhaust port as shown in FIG. 4B. Moreover, it is apparent that the arrangement depicted in FIG. 4B, in being concerned with a "deflation" as opposed to the "inflation" mode to startle the noenate, may dispense with the air reservoir 33. Thus, it is that the same is shown in FIG. 4B in dashed lines.

Figure 4C:
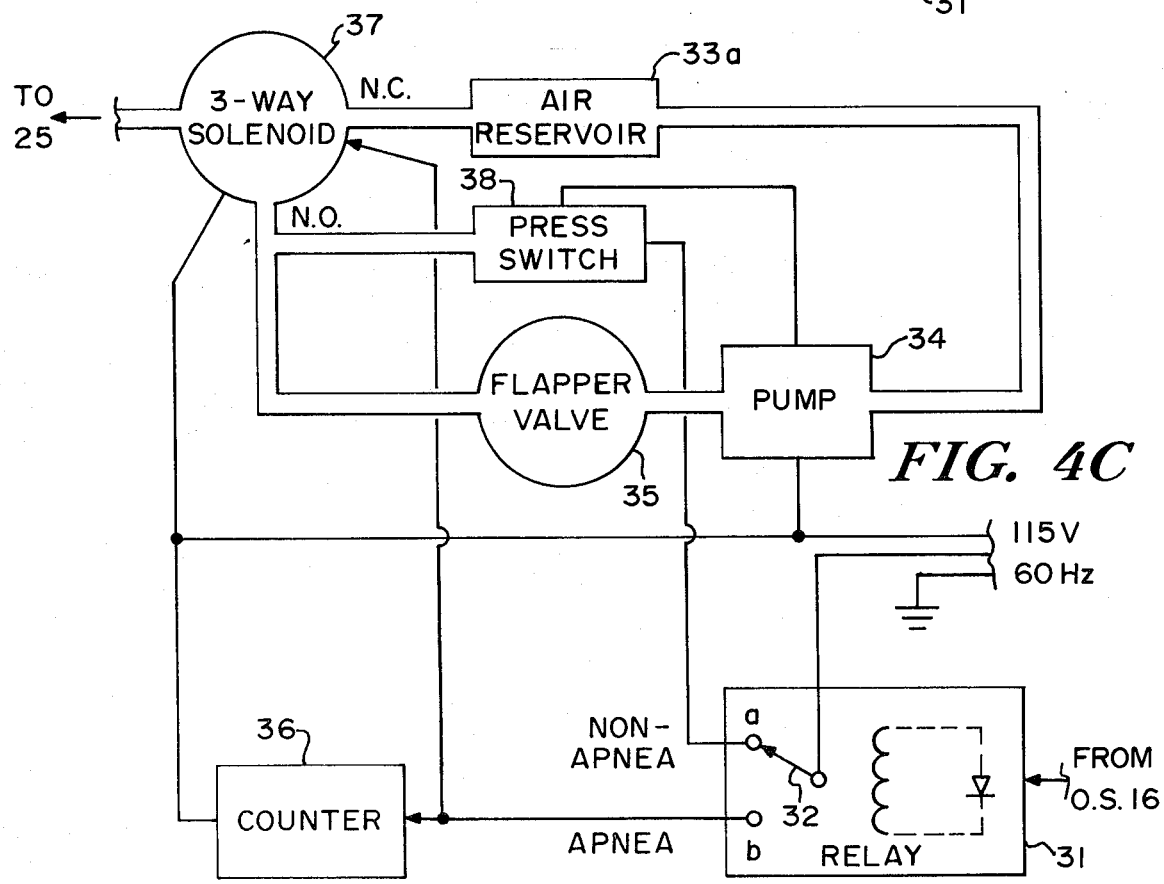
FIG. 4C is a schematic diagram in block form of yet another preferred embodiment of the unit 24 depicted in FIG. 1.

Yet a further embodiment of the pneumatic supply unit 24 is depicted in FIG. 4C, wherein it may be seen that a closed system is provided as between the pump 34, air reservoir 33a and pneumatic stimulator 25. Here again, the so-called "deflation" mode is applicable, wherein the initial or starting conditions of the pneumatic supply unit 24 are: that the pneumatic stimulator 25 is inflated to a prescribed or predetermined level; that three-way solenoid 37 is in its normal or rest mode which couples pneumatic stimulator 25 to the pump 34 via flapper valve 35; and that the pump, having inflated the mattress 25 to a predetermined level, has at the same time removed this air from reservoir 33a, thus, creating a partial vacuum therein. Now, when an apnea condition is detected and switch 32 changes over to the *b* position, three-way solenoid 37, in turn, responds to couple the inflated mattress 25 to the exhaust (normally closed) port which in turn permits a deflation of the mattress 25 into the vacuum condition created in air reservoir 33a. Thus, when the one-second period provided by one-shot 16 elapses and switch 32 returns to the *a* position, pressure switch 38 again detects a deflated mattress situation and responds by activating pump 34, which in turn evacuates air reservoir 33a as it supplies the air to the mattress 25 to once again return the system to its initial state. It is thus seen that this arrangement utilizes the same air over and over again and simultaneously evacuates the air reservoir 33a while the mattress is again being inflated, thereby achieving an entirely closed system.

In consideration of the possibility of untoward leakage in one side or the other (pressurized or evacuated sides) of the closed system, it is, of course, well within the scope of this invention to provide compensating means to sense the pressure inadequacy in either side and in response thereto supplement the initial pumping. Since the most critical factor is the requirement of the stimulator to sustain only a limited predefined internal pressure when inflated, this in turn becomes the limit which must not be exceeded by supplemental pumping via pump 34. It may be ensured that this upper pressure limit will not be exceeded by merely providing, for example, appropriate relief valve means appropriately preset.

Figure 5:
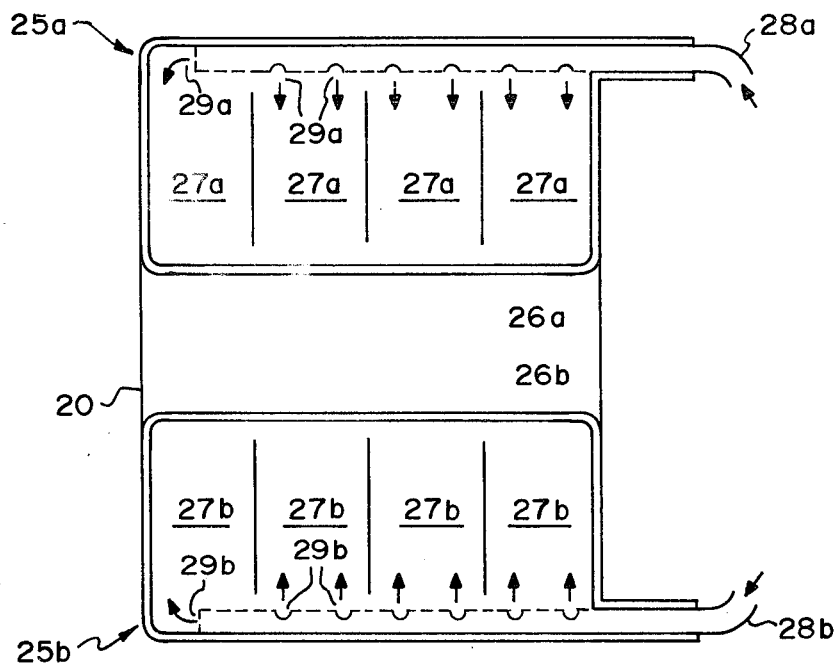
FIG. 5 is a top plan view of still another embodiment of a pneumatic stimulator 25.

Referring now to FIG. 5, there is seen therein a pair of mattresses 25a and 25b, which are shown to be the type of mattress embodied in FIG. 3A, but, which may, in fact, be the mattress embodiments depicted in FIGS. 3B or 3C. The dual mattress sections 25a and 25b are coupled together by a member 20 which may be composed of the same material as the mattress casings 26a and 26b. In fact member 20 may be comprised of a spongy or otherwise pillowy material to provide comfort to the neonate lying thereon. The intended mode of operation associated with a mattress configuration such as that depicted in FIG. 5 would have the neonate in essence lying between the dual mattress sections 25a and 25b such that the left and right sides of the head of the neonate are in actual contact with the dual sections 25a and 25b. This configuration is designed to provide a mechanical stimulus in the form of a rocking movement and sensation to the head of the neonate. One mattress section, e.g., 25a, is initially inflated, to be followed within a predetermined time period by mattress section 25b being inflated which, in turn, occurs at the same time that the first section 25a is being deflated, and so on. Thus, as the two mattress sections 25a and 25b are alternately inflated and deflated, the neonate's head is rocked back and forth gently but yet startlingly enough to arrest an apneic condition. It is contemplated that member 20 may be supplied with Velcro (Trademark) or a multiplicity of snaps (i.e., snap-in button arrangements) which would be arranged in two rows, one on either side thereof, which snaps or Velcro (Trademark) correspond to a row of mating snaps or Velcro (Trademark) on each of the dual mattress sections 25a and 25b. In this arrangement, member 20 is entirely removable from the mattress sections 25a and 25b, and a return to the mode of operation as, for example, depicted originally in FIGS. 3A and 4B may be effected. Moreover, it is contemplated that mattress sections 25a and 25b may be provided with several parallel rows of mating snaps so as to give the mattress configuration of FIG. 5 the provision of adjustability as to the width of separation between the mattress sections 25a and 25b. In this manner, the rocking mode mattress configuration can be tailored appropriately to the dimensions of the neonate.

Figure 6A:
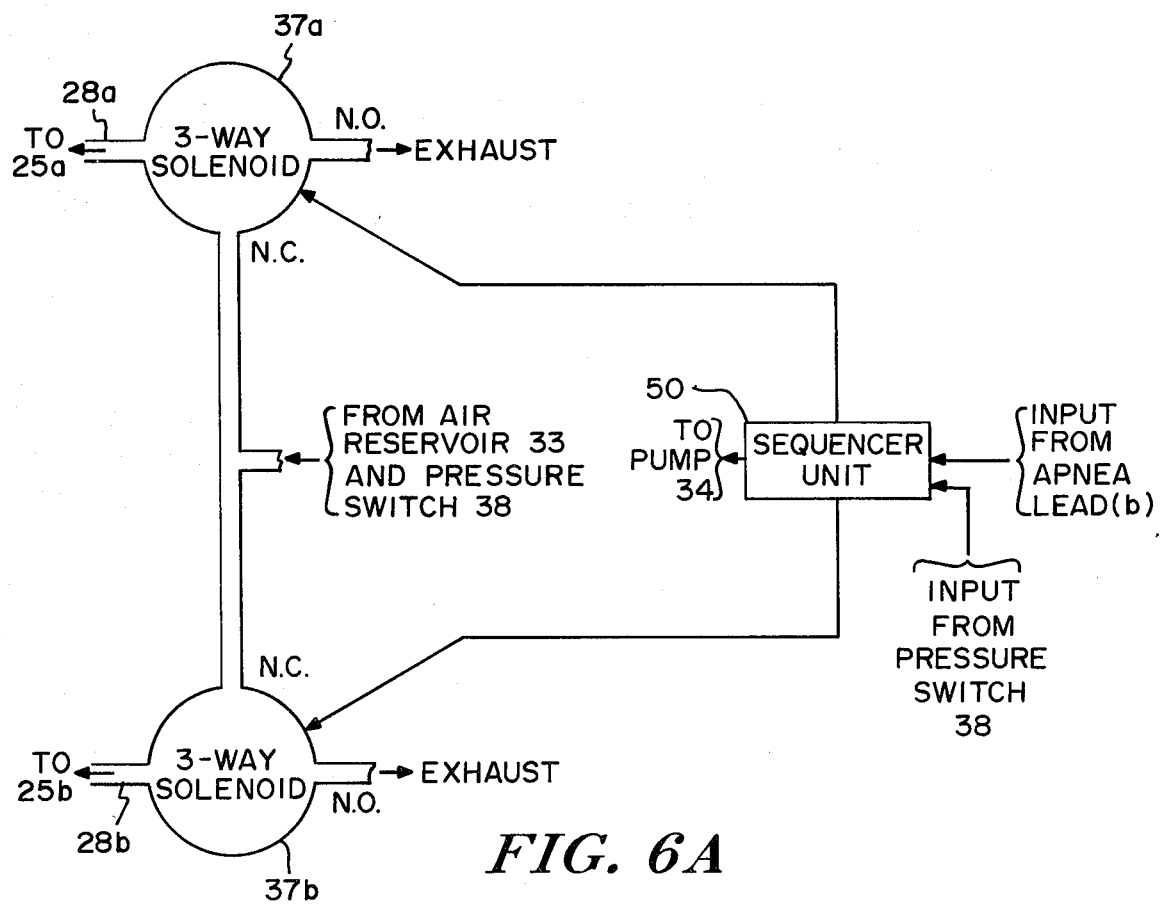
FIG. 6A is a schematic diagram of a pneumatic supply unit 24 designed to operate in conjunction with the stimulator depicted in FIG. 5.

An explanation of the "rocking mode" operation may be seen with reference to FIG. 6A, wherein a protion of the pneumatic supply unit 24 is shown. In this instance, air from the pump 34 is supplied to the reservoir 33 and to the normally closed ports of two three-way solenoids 37a and 37b, which, in turn, are coupled to the two mattress sections 25a and 25b via pneumatic tubes 28a and 28b respectively. Each of the three-way solenoids 37a and 37b are provided with a normally-opened exhaust port. Although the description hereof is mainly concerned with the "normally deflated mattress" mode, it will be appreciated that the mattress sections 25a and 25b could be partially inflated as one of the preset or starting conditions and that the rocking sensation be provided thereafter by the alternating deflation of said mattress sections. It will be appreciated that in the "normally inflated" mattress mode, there is less of a possibility of movement of the neonate to a position of reduced stimulation effectiveness.

The logic controlling the alternating inflation and deflation of the mattress sections 25a and 25b is provided by a sequencer unit 50 which takes the inputs supplied from apnea lead *b* and the pressure switch 38 and supplies appropriate electrical signals to the three-way solenoids 37a and 37b and to control the pump 34. While it is deemed that the sequencer unit may be of state of the art logic design capable of being implemented by one of ordinary skill in that art, the actual logic thereof is intended to be tailored to the actual kind and extent of the rocking mechanical stimulation, as well as the duration and intensity thereof. Therefore, one possible mode of operation as controlled by a particular sequencer unit logic is herein explained with reference to FIG. 6B, which illustrates a series of time-related pulse trains depicting the various signals controlled and supplied by the sequencer unit to effect a gentle rocking stimulus to the neonate. In this particular embodiment, it is deemed that the sequencer unit becomes fully operative off the normal one-second input pulse from lead *b*. While alternative consideration may be made that a second pulse from lead *b* may be needed sooner than shown in pulse train (a) of FIG. 6B, or may not be needed at all for the matter (apnea condition arrested on initial stimulation), the situation here illustrates a provision for a second input pulse from lead *b* to arrive, if needed, six seconds after the leading edge of the initial apnea or alarm pulse.

Figure 6B:
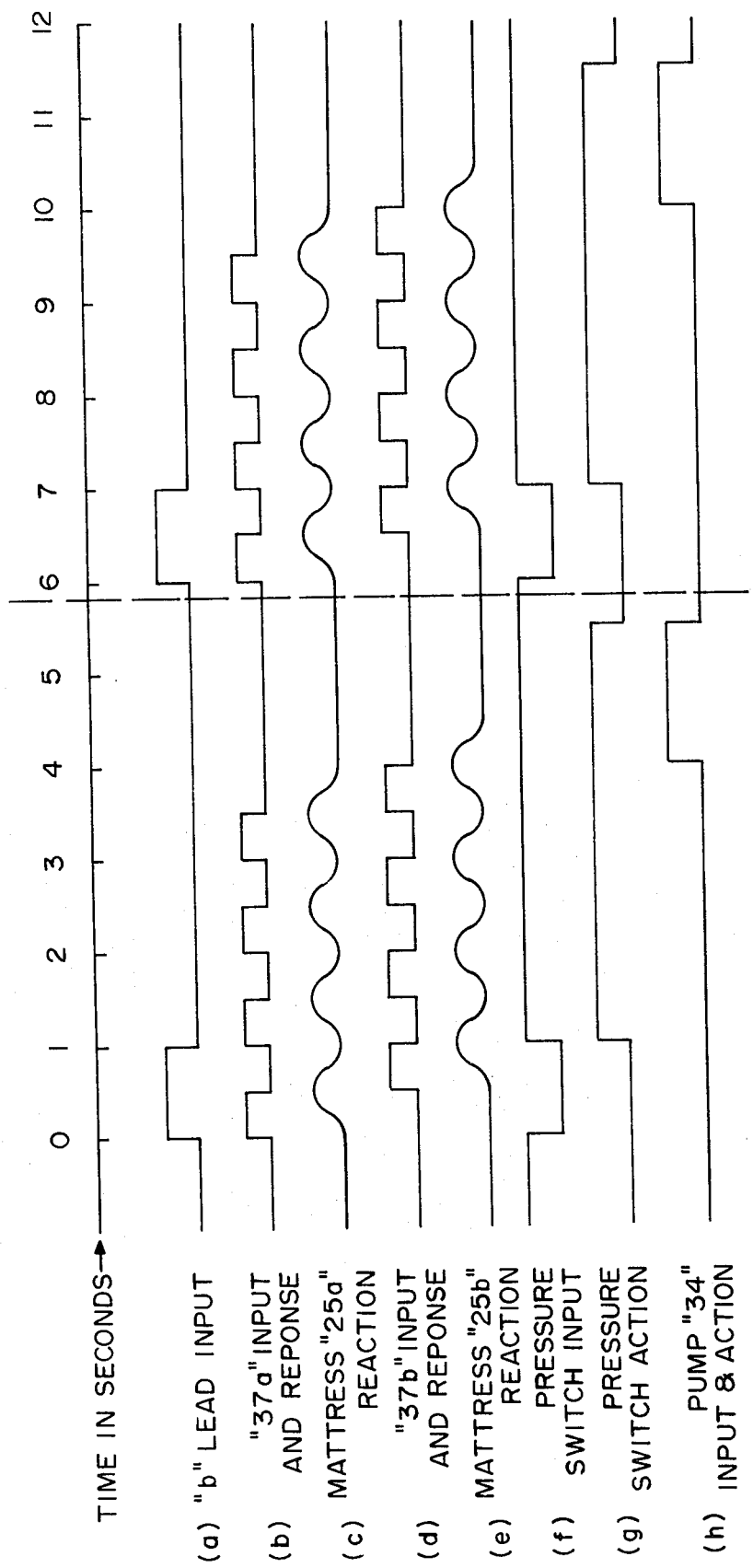
FIG. 6B is an operations chart illustrating as a function of time the functioning of the arrangement of FIG. 6A as controlled by the respiratory unit provided therein.

As a result of receiving the input from lead *b* sequencer unit 50 provides an output signal pulse train to three-way solenoid 37a wherein the latter reacts in the functioning sequence as shown in part (b) of FIG. 6B. This functioning response is comprised of four complete cycles, i.e., the mattress section 25a in four successive instances is alternately coupled to the exhaust port of element 37a and then recoupled to the air reservoir 33. As a result, the mattress section 25a periodically inflates at one-second intervals as depicted in part (c) of FIG. 6B. Contemporaneous therewith, but delayed by one-half of a second, mattress 37b is in the same manner periodically inflated and deflated under the control of sequencer unit 50, as depicted in parts (d) and (e) of FIG. 6B. The overall result of this mode of operation is that while one mattress section is inflating the other is deflating and vice-versa, thus causing the head of the neonate to be rocked gently back and forth four times in succession.

Part (f) of FIG. 6B depicts the pressure switch 38 input from terminal *a* of switch 32. It will be noted that power is supplied to the pressure switch input throughout except when switch 32 is switched to position *b*, as may be seen from part (a) of FIG. 6B. Notwithstanding the pressure switch input, however, the output thereof leading to pump 34 is controlled by sequencer unit 50 such that even though the pressure switch 38 would normally attempt to supply input power to the pump 34 as shown in part (g) of FIG. 6B, sequencer unit 50 prevents the pump from being activated until the end of the four successive rocking cycles, which correspondingly, terminates at the end of the fourth second following the leading edge of the input signal from lead *b*. The pump as controlled be sequencer unit 50 remains "on" for an adjustable period of about 1½ seconds and which may be varied up to a maximum of just under two seconds. The time of running of the pump is here essentially governed by two factors: (1) the need for the air reservoir to be again filled to the predetermined pressure level for providing sufficient air pressure to effect a full four-cycle rocking mode without any substantial damping of the system activity; and (2) the arrival of a second pulse from one-shot 16, indicating that a second rocking stimulation is needed to arrest an apnea condition. As FIG. 6B shows, the rocking sequence would be repeated upon the arrival of such a second input pulse at lead *b*. Thus, by this system if an apnea condition persists after the first 6 seconds, a secondary attempt is made to stimulate the neonate via rocking. Of course, if a second rocking episode fails to arrest the apnea condition, further alarms, perhaps, having different sounds from the initial alarm which accompanied the determination of an apnea condition, could then be initiated and thereby immediately call to the awareness of the nurse or other attendant the failure to arrest the apneic condition of the monitored neonate.

It is noted that sequencer 50 may provide the control functions as depicted, in for instance, in FIG. 6B, by either electronic or mechanical switching, which is controllable either mechanically, for example, by a camming arrangement, or electronically, for example, via an arrangement including a state of the art multivibrator clock arrangement, which runs for a set time period following an input trigger from input lead *b*.

It is, moreover, to be particularly noted that the rocking mode arrangement such as is depicted in FIGS. 6A and 6B, in conjunction with the mattress arrangement according to FIG. 5, avoids the potential problem of a neonate going into the condition known as laryngospasm, simply by the fact that the stimulus is a gentle but sufficiently starting rocking motion.

It is to be further noted that the control functions of the sequencer 50 in a rocking-mode arrangement could be provided by a mini-processor wherein the times of inflation and deflation of the mattress sections 25*a* and 25*b*, as well as the height of inflation and extent of deflation thereof may be automatically variable in accordance with the effect of the stimulus provided so as to vary the overall rocking motion accordingly.

There exists, of course, the possibility of combining several of the embodiments disclosed hereinabove, such as, for example, providing a system employing the rocking mode of operation together with a third mattress section which is placed under the neck of the neonate. In this arrangement, the initial mode of stimulation could be a rocking mode, and, if the same was unsuccessful in arresting an apnea condition, the sequencer unit could be fed with a second signal from the *b* lead of switch 32. This second signal would be intepreted by the sequencer unit as a failure to arrest the initial apnea condition and which in turn would bring into action the third mattress section lying under the neck of the neonate, wherein this third section would then inflate (or deflate) to stimulate the neonate via the falling-sensation mode. Of course, an integral mattress arrangement may be provided with these three sections being held together by an element similar to member 20. In conjunction therewith, a multiconduit tubing may be used to cut down on the number of separate pneumatic leads running to and from the mattress.

While the principles of this invention have been described in connection with specific examples of apparatus, it is to be understood that such examples are not to be considered as limiting the scope of this invention or the claims appended hereto.

I claim:
1. A patient care system for monitoring and treating respiratory distress problems, comprising:
   a. first means for sensing respiratory activity and generating electrical signals corresponding thereto;
   b. second means responsive to said respiratory activity signals for detecting a respiratory distress problem; and
   c. stimulating means, including fluid-inflatable means adapted for placement under a patient, and responsive to said second means for inducing a startling loss of equilibrium in the patient through a rapid momentary lowering action of a non-oscillatory type of said fluid-inflatable means.

2. The system according to claim 1 wherein said fluid-inflatable means is normally inflated to a predetermined extent, and said stimulating means further includes fluid supply and control means, electrically coupled to said second means and pneumatically coupled to said fluid-inflatable means, for causing a rapid momentary deflation of said fluid-inflatable means in response to a detection of a respiratory distress problem.

3. The system according to claim 2 wherein said stimulating means comprises a closed pneumatic system which includes means for simultaneously inflating said fluid-inflatable means to said predetermined extent and preparing a partially evacuated exhaust path adapted for assisting the rapid momentary deflation of said fluid-inflatable means.

4. The system according to claim 3 wherein said fluid supply and control means includes fluid reservoir means operatively coupled to said fluid-inflatable means and pumping means operatively coupled between said fluid-inflatable means and said fluid reservoir means.

5. The system according to claim 4 wherein said fluid supply and control means includes means for maintaining a predetermined fluid pressure for inflating said fluid-inflatable means.

6. The system according to claim 4 wherein said stimulating means further includes pneumatic switching means operatively coupling said fluid reservoir means and said pumping means to said fluid-inflatable means, whereby in response to a respiratory distress condition being detected by said second means, said pneumatic switching means is caused to directly couple said predeterminably-inflated fluid-inflatable means to said fluid reservoir means, the latter comprising said partially evacuated exhaust path, and thereby enable a rapid momentary deflation of said fluid-inflatable means.

7. The system according to claim 6 wherein said stimulating means includes timing means for causing said pressure-controlled switching means, following a predetermined time period in which said fluid-inflatable means is deflated, to couple said fluid-inflatable means to said pumping means and for actuating the latter and thereby reinflate said fluid-inflatable means to said predetermined fluid pressure level while simultaneously re-evacuating said fluid reservoir means.

8. The system according to claim 7 wherein said stimulating means further includes pressure-controlled switching means pneumatically coupled to said fluid-inflatable means and electrically coupled to said pumping means for causing the latter to be actuated upon the occurrence of a predetermined fluid pressure threshold being reached within said fluid-inflatable means.

9. A patient care system for monitoring and treating respiratory distress problems, comprising:
   a. first means for sensing respiratory activity and generating electrical signals corresponding thereto;
   b. second means responsive to said respiratory activity signals for detecting a respiratory distress problem; and
   c. stimulating means, including dual fluid-inflatable means each being adapted for placement on either side of and partially extending under a patient and third means for causing controlled alternate inflation and deflation of said dual fluid-inflatable means, and responsive to said second means for inducing a startling loss of equilibrium in the patient through a relatively rapid momentary rocking motion of a preselected portion of the patient's body by the alternate inflation and deflation of said dual fluid-inflatable means.

10. The system according to claim 9 wherein said third means includes fluid supply and control means coupled to said detecting means for predeterminably inflating and deflating said dual fluid-inflatable means periodically.

11. The system according to claim 10 wherein said fluid supply and control means includes fluid reservoir means for maintaining a predetermined fluid pressure for inflating said dual fluid-inflatable means.

12. The system according to claim 10 wherein said dual fluid-inflatable means comprises an inflatable pneumatic unit which includes a pair of inflatable mattresses adjustably coupled together to provide predetermined separation therebetween, each of said pair of mattresses being adapted to be situated on either side of, and extend partially under, a preselected portion of the patient.

13. The system according to claim 12 wherein said fluid supply and control means includes means for alternately inflating and deflating said pair of inflatable mattresses for a predetermined duration in a cyclic pattern following the detection of a respiratory distress situation.

14. The system according to claim 13 wherein said means for alternately inflating and deflating said pair of inflatable mattresses includes a pair of pneumatic switching means intercoupled to a pressurized fluid source and fluid motive means, each of said pair of pneumatic switching means being coupled additionally to one of said inflatable mattresses, and control means coupled to said detecting means and to each of said pair of pneumatic switching means, for causing in response to the detection of a respiratory distress problem said pair of pneumatic switching means to alternately be actuated in a switching sequence having predetermined timing and duration, and for causing in response thereto each of said pair of mattresses to be correspondingly coupled alternately to the pressurized fluid source and then to an exhaust, with the switching sequence of the one switching means and the inflatable mattress associated therewith being delayed by a predetermined portion of the period of a switching cycle relative to the other of said pair of pneumatic switching means and its associated inflatable mattress.

15. The system according to claim 14 wherein said control means includes means for providing a predetermined termination of the switching sequence prior to the earliest possible arrival time of a second indication of respiratory distress, and thereby effect an interval of switching inactivity of predetermined minimal duration preceding the arrival of said earliest possible second indication of respiratory distress.

16. The system according to claim 9 wherein said dual fluid-inflatable means include means configured to be in cooperative relationship to the patient's body for effectively causing a falling sensation to be imparted alternately to either side of the preselected portion of the patient's body.

* * * * *